United States Patent [19]

Crivello

[11] Patent Number: 4,675,426
[45] Date of Patent: Jun. 23, 1987

[54] FREE-RADICAL, INITIATORS, CURABLE COMPOSITIONS, AND METHODS

[75] Inventor: James V. Crivello, Clifton Park, N.Y.

[73] Assignee: General Electric Company, Schenectady, N.Y.

[21] Appl. No.: 872,983

[22] Filed: Jun. 11, 1986

[51] Int. Cl.$^4$ ............................ C07F 7/08; C07F 7/18
[52] U.S. Cl. .................................... 556/464; 526/194; 524/107; 524/265; 524/267
[58] Field of Search ....................... 556/464; 526/194; 524/107, 265, 267

[56] References Cited

U.S. PATENT DOCUMENTS 4,535,174  8/1985  Crivello .......................... 556/464 X

*Primary Examiner*—Paul F. Shaver
*Attorney, Agent, or Firm*—William A. Teoli; James C. Davis, Jr.; James Magee, Jr.

[57] ABSTRACT

There is provided curable compositions of free-radical polymerizable organic monomers and polymers and cyclicsilylpinacoles which can be used in combination to make such curable compositions.

13 Claims, No Drawings

FREE-RADICAL, INITIATORS, CURABLE COMPOSITIONS, AND METHODS

BACKGROUND OF THE INVENTION

Prior to the present invention, benzopinacole and other tetraarylethanes having the formulas

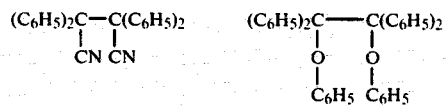

have been used as high temperature free radical initiators for the polymerization of vinyl monomers. Additional free radical initiators useful for vinyl monomer polymerization are the corresponding trialkylsilylether derivatives of benzopinacole, shown by the formula,

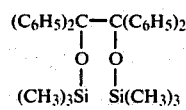

disclosed by Rudolph et al, U.S. Pat. Nos. 3,391,355 and Vio, 3,792,126. Oligomeric silyl pinacoles also shown to be useful as free radical vinyl monomer initiators are shown by Wolfers et al, Offenlegungsschrift No. 2,632,294 and Reuter et al, Offenlelegungsschrift No. 3,151,444.

There also is shown in U.S. Pat. No. 4,535,174, Free-Radical Initiators and Method for Making, assigned to the same assignee as the present invention and incorporated herein by reference. These free-radical initiators are in the form of silyl ethers of aryl pinacoles based on the reaction of an aryl ketone with a monohalo- or dihalo-silane having at least one olefinically unsaturated organic radical attached to silicon, in the presence of an active metal reducing agent, such as magnesium. The free-radical initiators of U.S. Pat. No. 4,535,174 have been found to be valuable as intermediates in the production of polydiorganosiloxanes having terminal or innerchain silyl pinacole functional groups.

It has now been discovered that cyclic silyl pinacoles having the formula

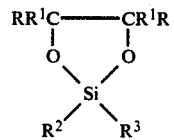

are a class of highly efficient free-radical initiators with potential applications for the polymerization of vinyl monomers, the cure of unsaturated polyesters and for the cross-linking of polyolefins, where R and $R^1$ are the same or different $C_{(6-14)}$ aromatic organic radicals, and when joined together and attached to the same carbon atom are selected from divalent aryl radicals having the formula

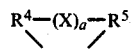

$R^4$ and $R^5$ are selected from divalent $(C_{6-14})$aryl organic radicals, $R^2$ is a monovalent radical selected from $C_{(1-8)}$ alkyl, $C_{(1-8)}$ alkenyl, $C_{(1-8)}$ haloalkyl, $C_{(1-8)}$ alkoxy, or $C_{(6-13)}$ aryl, $R^3$ is a monovalent radical selected from hydrogen and $R^2$ radicals, X is selected from O, S, $CH_2$, and $$\overset{O}{\underset{}{\overset{\|}{C}}},$$

and a is 0 or 1.

Radicals included within R and $R^1$ or Formula 1 are, for example, phenyl, tolyl, xylyl, naphthyl, chlorophenyl, methoxy, nitrophenyl, etc. Radicals included within $R^2$ are, for example, methyl, ethyl, propyl, butyl, etc.; chloroethyl, methoxy, ethoxy, vinyl, aryl, such as phenyl, tolyl, xylyl, naphthyl, etc. Radicals included within $R^3$ are, for example, $R^2$ radicals and hydrogen. Radicals included within $R^4$ and $R^5$ are phenylene, tolylene, xylylene, naphthylene, and substituted derivatives thereof.

STATEMENT OF THE INVENTION

There is provided by the present invention curable compositions comprising (A) 100 parts of a free radical polymerizable organic monomer, polymer or mixture thereof, and (B) 0.1 to 20 parts of a silyl pinacole of Formula 1.

There are included among the silyl pinacoles of Formula 1 which can be utilized in the practice of the present invention as free-radical initiators compounds such as

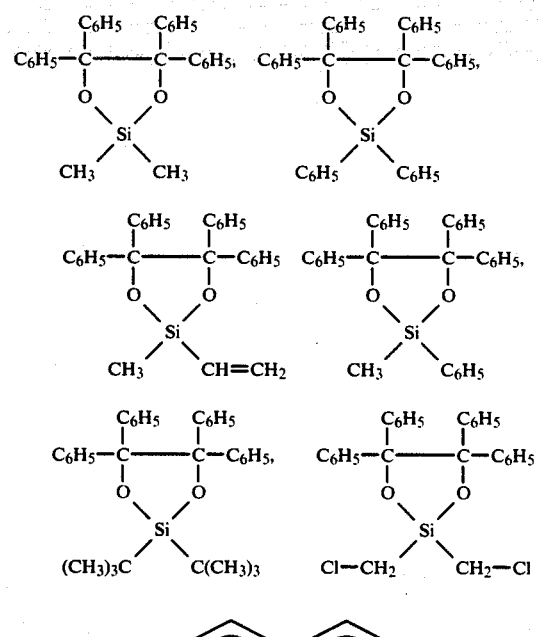

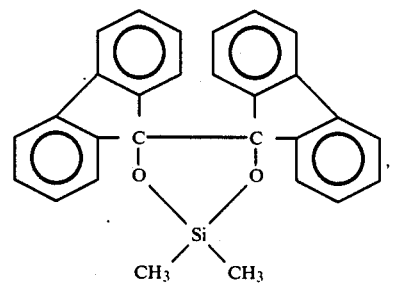

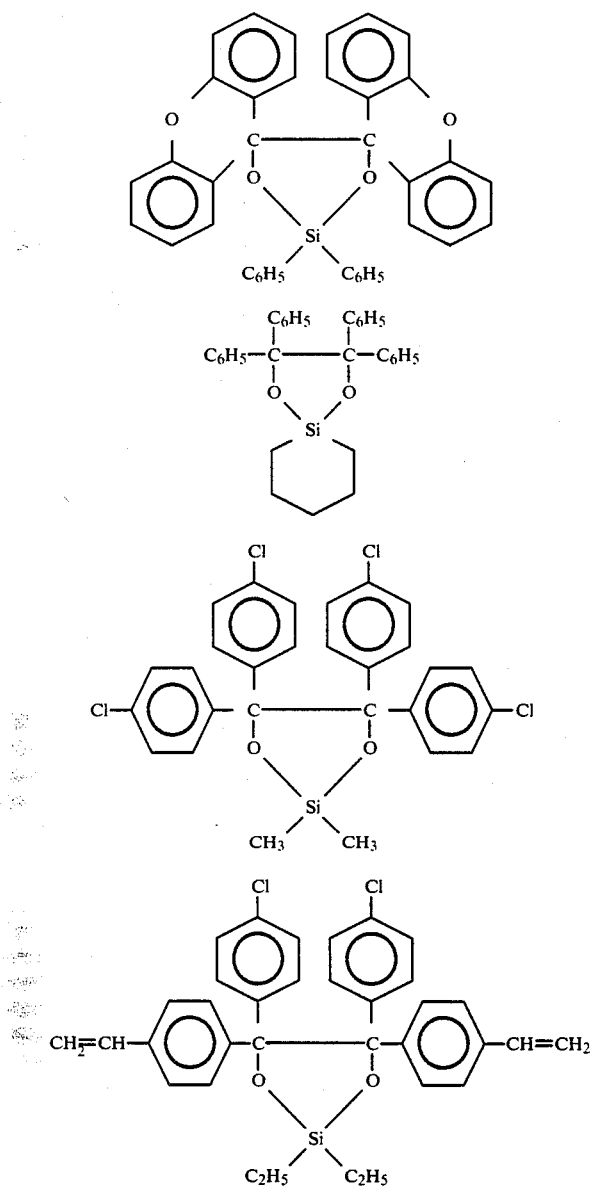

Among the free-radical polymerizable organic monomers which can be utilized in the practice of the present invention to make the durable compositions, there are included styrene, 4-methylstyrene, 4-chlorostyrene, 2-bromostyrene, 1,4-divinylbenzene, methylmethacrylate, n-butylacrylate, diallylphthalate, 1,6-hexanedioldiacrylate, neopentylglycoldiacrylate, Bisphenol-A-dimethacrylate.

Free radical polymerizable organic polymers which can be used in the practice of the present invention in combination with the silyl pinacolates of Formula 1 are, for example, styrenated unsaturated polyesters, diallylcarbonate resins, maleimide resins, acrylated epoxy resins, copolymers of styrene and butadiene or isoprene, copolymers of ethylene or propylene and butadiene.

One method of making the silyl pinacoles of Formula 1 is by affecting reaction between an aryl ketone, for example, benzophenone with a diorganodihalosilane or diorganomonohalosilane in the presence of an active metal such as magnesium. Typical arylketones which can be used in addition to diphenylketone are, for example, 9-fluorenone, 4,4'-dichlorobenzophenone, thioxanthone, anthrone, 4,4'-dimethoxybenzophenone.

Some of the diorganodihalosilanes which can be used are, for example, halosilanes such as chlorosilanes having $C_{(1-14)}$ hydrocarbon radicals attached to silicon by carbon-silicon linkages such as $C_{(1-8)}$ alkyl radicals, for examples, methyl, ethyl, propyl, butyl, pentyl, and $C_{(6-14)}$ aromatic hydrocarbon radicals such as phenyl, tolyl, xylyl, naphthyl, etc. Typical diorganodihalosilanes are, for example, dimethyldichlorosilane, diethyldichlorosilane, ethylmethyldichlorosilane, methylphenyldichlorosilane, diphenyldichlorosilane, di-t-butyldichlorosilane.

The above reaction between the diarylketone and magnesium and the diorganodihalosilane can be conducted in the presence of organic solvents such as tetrahydrofuran and diethylether, dioxane, N,N,N',N'-tetramethylethylene diamine, 1,2-dimethoxyethane, 2-methoxyethyl ether, in the presence of an effective amount or a promoter, for example, hexamethylphosphoramide, tetramethylurea to accelerate the reaction. The promoter can be utilized in an amount equivalent to about 0.5% to 10% by weight of the reaction mixture. Temperatures which can be used are, for example, 0° C. to 100° C. under substantially anhydrous conditions, for example under a nitrogen atmosphere.

It has been further found that in place of the above diorganodihalosilane there can be used a diorganohalosilane, for example, dimethylchlorosilane or other diorganohalosilane equivalent to the above-described diorganodihalosilane except that a hydrogen atom is attached to silicon in place of a halogen radical. Typical diorganomonohalosilanes are: dimethylchlorosilane, methylphenylchlorosilane, diphenylchlorosilane, ethylmethylchlorosilane, and methylchloromethyl chlorosilane.

Another procedure which can be used to produce the silylpinacoles of Formula 1 involve the use of the above-described procedure of utilizing two moles of arylketone and one mole of magnesium in the presence of hydrocarbon solvent, such as toluene and an effective amount of mercury dichlorides such as a 0.5 to 10% by weight of mercury dichloride based on the weight of the reaction mixture. It has been found that the corresponding magnesium pinacolate salt is formed which thereafter can be reacted with the appropriate diorganodihalosilane or diorganohalosilane as previously described to produce the pinacolate salt within the scope of Formula 1. Another procedure which can be used to make the cyclic silylpinacolate within the scope of Formula 1 is by affecting reaction between a pinacole such as benzopinacole or other aromatic pinacoles such as 9-fluorenonepinacole, 4,4'-dichlorobenzophenone pinacole 4,4'-dimethoxybenzophenone pinacole, thioxanthone pinacole, with a diorganodihalosilane or diorganohalosilane as previously defined in the presence of an effective amount of a trialkylamine as an acid acceptor. An effective amount of trialkylamine is, for example, a substantially stoichiometric equivalence of trialkylamine which is equivalent to the amount of hydrogenhalide generated during the reaction. In instances where a diorganohalosilane is employed, hydrogen evolution can result.

The curable compositions of the present invention can be made by incorporating the silylpinacoles of Formula 1, such as dissolving them in an appropriate free radical polymerizable organic monomer or polymer. It has been found that graft copolymers can be made such as grafting maleic anhydride onto polyethylene utilizing the cyclic silylpinecoles of Formula 1 because these materials have a significantly higher thermal stability than presently available free-radical initiators. Additional graft copolymer reactions are, for example, polyethylene-graft-styrene, polystyrene-graft-maleic anhydride, poly-2,6-dimethyl-1,4-phenylene, oxide-graft-maleic anhydride, polypropylene-graft-acrylonitrile, cellulose-graft-styrene, polyethylene-graft-vinyltrimethoxysilane.

In order that those skilled in the art will be better able to practice the present invention, the following examples are given by way of illustration and not by way of limitation. All parts are by weight.

EXAMPLE 1

A mixture was stirred for 12 hours under substantially anhydrous conditions under nitrogen consisting of 18.2 grams (g) (0.1 mole) of benzophenone, 50 mL of tetrahydrofuran, 12.9 g (0.1 mole) of dimethyldichlorosilane, 1.2 g magnesium metal, and 5 mL of hexamethylphosphoramide. The tetrahydrofuran was removed with the aid of a rotary evaporator and approximately 100 mL of methylene chloride was added to the mixture and the solution filtered through a sintered glass filter to remove the magnesium salts. The filtrate was then stripped under reduced pressure leaving a solid residue. The residue was crystallized from absolute ethanol giving a colorless crystalline product having a melting point of 134°–136° C. after drying at 6° C. in vacuo. The product was identified as 2,2-dimethyl-4,4,5,5-tetraphenyl-1,3-dioxa-2-silole based on its proton and $^{13}$C-NMR spectra as well as by the parent peak at M/e=435 and its elemental analysis.

An alternate procedure was used to prepare the same cyclic silylpinecole. There was added 50 mL tetrahydrofuran to a fluid which was being stirred under a nitrogen atmosphere consisting of 4.8 g (0.2 mole) magnesium metal, 9.1 g (0.05 mole) benzophenone and 2.4 g (0.009 mole) of mercuric chloride. A rapid exotherm ensued with the temperature rising to the boiling point of the tetrahydrofuran. The reaction appeared to be over in 15 minutes and 9.9 g (0.1 mole) of dimethylchlorosilane was added to the solution with stirring. Another exothermic reaction took place and the temperature was controlled with the aid of a water bath. The mixture was allowed to stir for 5 minutes after completing the addition of the silane, then 100 mL ethylether was added to precipitate the magnesium salts. The reaction mixture was filtered through a sintered glass filter and the filtrate placed in a rotary evaporator to remove the solvents. There was obtained a colorless crystalline solid which was washed several times with absolute ethanol. Based on method of preparation and proton NMR and $^{13}$C-NMR, there was obtained a 54% yield of 5.8 g of the above cyclic silyl pinacolate.

There was obtained a 33.2% yield of the same cyclic silyl pinacolate utilizing a similar reaction with dimethylchlorosilane, magnesium metal benzophenone, and 5 mL of tetramethylurea as reagents.

EXAMPLE 2

Following the procedure of Example 1, there was combined 18.2 parts (0.1 mole) of benzophenone, 1.2 g (0.05 mole) of magnesium, 12.6 g (0.05 mole) diphenyldichlorosilane, and 50 mL of dry tetrahydrofuran. There was added to the aforementioned solution, 5 mL of tetramethylurea. After reaction and workup as previously described in Example 1, followed by recrystallization from isopropanol, there was obtained 9.5 g of 2,2-diphenyl-4,4,5,5-tetraphenyl-1,3-dioxy-2-silole as a colorless crystalline solid.

EXAMPLE 3

The procedure of Exmaple 2 was repeated, except there was used 7.83 g (0.05 mole) of methylphenylchlorosilane. There was obtained a white solid which could be further purified by recrystallization from nitromethane. The product had a melting point of 150°–151° C. Based on method of preparation, $^{13}$C-NMR and elemental analysis, the product was 2-methyl-2-phenyl-4,4,5,5-tetraphenyl-1,3-dioxa-2-silole.

EXAMPLE 4

There was added drop-wise 5.05 g (0.05 mole) of triethylamine to a mixture while it was being stirred under a nitrogen atmosphere of 18.3 g (0.05 mole) benzopinacole, 4.7 g (0.05 mole) dimethylchlorosilane, and 50 ml of chloroform. An exothermic reaction together with vigorous gas evolution resulted. The reaction mixture was stirred for two hours after the addition had been completed. Under reduced pressure, the solvent was removed and a white solid was obtained which was extracted with hexane. Based on method of preparation and its elemental analysis, the product was a cyclic silyl benzopinacole, as shown in Example 1. The following table shows the characteristics of various cyclic silylpinacoles made in accordance with the above procedures:

CYCLIC SILYLPINACOLES

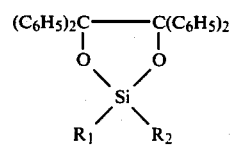

| $R_1$ | $R_2$ | m.p. (°C.)$^a$ | $^{29}Si^\delta$ (ppm)$^b$ | M.W. | | % C | % H | % Si |
|---|---|---|---|---|---|---|---|---|
| CH$_3$ | CH$_3$ | 134–136 | 20.82 | 422.6 | Calc: | 79.58 | 6.20 | 6.64 |
| | | | | | Fnd: | 79.31 | 6.5 | 6.7 |
| C$_2$H$_5$ | C$_2$H$_5$ | 123–125 | 19.16 | 450 | Calc: | 79.95 | 6.71 | 6.23 |
| | | | | | Fnd: | 79.77 | 6.67 | 6.2 |
| C$_6$H$_5$ | C$_6$H$_5$ | >200 | −9.51 | 546 | Calc: | 83.48 | 5.53 | 5.14 |
| | | | | | Fnd: | 83.38 | 5.47 | 4.97 |

CYCLIC SILYLPINACOLES

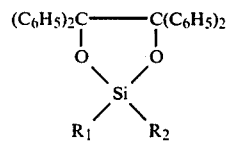

| $R_1$ | $R_2$ | m.p. (°C.)[a] | $^{29}Si^\delta$ (ppm)[b] | M.W. | Elemental Analysis | % C | % H | % Si |
|---|---|---|---|---|---|---|---|---|
| $CH_3$ | $CH_2=CH$ | 135–137 | 4.68 | 434.6 | Calc: | 80.14 | 6.03 | 6.46 |
|  |  |  |  |  | Fnd: | 79.97 | 6.09 | 6.34 |
| $CH_3$ | $C_6H_5$ | 150–151 | 5.22 | 484 | Calc: | 81.82 | 5.79 | 5.79 |
|  |  |  |  |  | Fnd: | 81.60 | 5.76 | 5.80 |
| $(CH_3)_3C$ | $(CH_3)_3C$ | 185–199 | 12.59 | 506.7 | Calc: | 80.58 | 7.56 | 5.53 |
|  |  |  |  |  | Fnd: | 80.16 | 7.41 | 5.03 |

[a] = Melting is accompanied by decomposition
[b] = $^{29}Si$ NMR run in $CDCl_3$

EXAMPLE 5

A curable mixture consisting of about 70% by weight of unsaturated polyester, 30% by weight of styrene and 2% by weight of cyclic silylpinacole of Example 1 was evaluated with a Sunshine Gel Timer at temperatures of about 120° C. The unsaturated polyester consisted essentially of a reaction product of fumaric acid, neopentylgycol, tetrahydrophthalic anhydride and propyleneglycol. There was obtained a gel time of 7.5 minutes.

EXAMPLE 6

A polymerization of a mixture of 4.8 g of freshly distilled styrene and 0.1224 g of 2,2-dimethyl-4,4,5,5-tetraphenyl-1,3-dioxa-2-silole was evaluated in a steel tube flushed with nitrogen at 80° C. for 40 minutes. The resulting solution was poured into methanol and the product precipitated was isolated by filtration. There was obtained 1.43 g or 30% conversion of polystyrene having a number average of molecular weight of 80,400 g/mole and a weight average molecular weight of 280,100 g/mole.

EXAMPLE 7

There were added 4.9 g of maleic anhydride and 2.1 g of 2,2-dimethyl-4,4,5,5-tetraphenyl-1,3-dioxa-2-silole to a solution at 140° C. of 14 g of polyethylene (low density) and 100 mL of 1,2-dichlorobenzene. The resulting mixture was heated with stirring at 140°–150° C. for 4 hours. The mixture was then poured into methanol to precipitate the polymer. Methanol was poured off and the polymer was extracted with a large volume of fresh methanol. The polymer was isolated by filtration and the polymer thoroughly washed with methanol. After drying for four days at 40° C. in vacuo, there was obtained 14.58 g of the product. Based on method of preparation and its infrared spectrum, the product was a graft copolymer showing bands at 1850 $cm^{-1}$ and 1775 $cm^{-1}$, establishing the presence of grafted maleic anhydride groups.

Although the above examples are directed to only a few of the very many variables which can be utilized in the practice of the method of the present invention and compositions obtained therefrom, it should be understood that the curable compositions of the present invention are directed to a much broader variety of materials shown by the unsaturated monomers and polymers and cyclicsilylpinacoles shown in the description preceding these examples. A preferred class of cyclic silyl pinacoles having the following formula

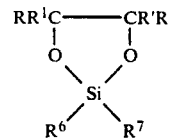

where R and $R^1$ are as previously defined, $R^6$ is selected from monovalent $C_{(1-14)}$ hydrocarbon radical free of aliphatic unsaturation, and $C_{(1-14)}$ monovalent hydrocarbon radical free of aliphatic unsaturation substituted with radicals neutral during free radical polymerization, and $R^7$ is selected from hydrogen and $R^6$.

What is claimed and sought to be protected by Letters Patent of the United States is as follows:

1. Curable compositions comprising (A) 100 parts of a free radical polymerizable organic monomer, polymer or mixture thereof, and (B) 0.1 to 20 parts of a silyl pinacole of the formula

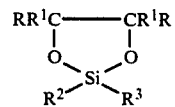

where R and $R^1$ are the same or different $C_{(6-14)}$ aromatic organic radicals, and when joined together and attached to the same carbon atom are selected from divalent aryl radicals having the formula

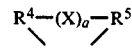

$R^4$ and $R^5$ are selected from divalent $(C_{6-14})$ aryl organic radicals, $R^2$ is a monovalent radical selected from $C_{(1-8)}$ alkyl, $C_{(1-8)}$ haloalkyl, $C_{(1-8)}$ alkoxy, or $C_{(6-13)}$ aryl, $R^3$ is a monovalent radical selected from hydrogen and $R^2$ radicals, X is selected from O, S, $CH_2$ and

and a is 0 or 1.

2. A curable composition in accordance with claim 1 where the free-radical polymerizable organic monomer is styrene.

3. A curable composition in accordance with claim 1 where the free-radical curable polymerizable organic polymer is an unsaturated polyester.

4. A curable composition in accordance with claim 1 where the cyclicsilylpinacole is 2,2-dimethyl-4,4,5,5-tetraphenyl-1,3-dioxa-2-silole.

5. A curable composition in accordance with claim 1, having a mixture of polyethylene and styrene.

6. A curable composition in accordance with claim 1, having a mixture of maleic anhydride and polyethylene.

7. Cyclic silyl pinacoles of the formula

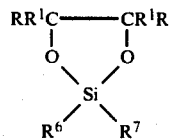

where R and $R^1$ are the same or different $C_{(6-14)}$ aromatic organic radicals, and when joined together and attached to the same carbon atom are selected from divalent aryl radicals having the formula

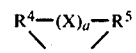

$R^4$ and $R^5$ are selected from divalent $(C_{6-14})$ aryl organic radicals, $R^6$ is selected from monovalent $C_{(1-14)}$ hydrocarbon radical free of aliphatic unsaturation, and $C_{(1-14)}$ monovalent hydrocarbon radical free of aliphatic unsaturation substituted with radicals neutral during free radical polymerization, and $R^7$ is selected from hydrogen and $R^6$, X is selected from O, S, $CH_2$ and

and a is 0 or 1.

8. A cyclic silyl pinacole in accordance with claim 7, where R and $R^1$ are phenyl and $R^6$ and $R^7$ are methyl.

9. A cyclic silyl pinacole in accordance with claim 7, where R and $R^1$ are phenyl and $R^6$ and $R^7$ are ethyl.

10. A cyclic silyl pinacole in accordance with claim 7, where R and $R^1$ are phenyl and $R^6$ and $R^7$ are phenyl.

11. A cyclic silyl pinacole in accordance with claim 7, where R and $R^1$ are phenyl and $R^6$ and $R^7$ are t-butyl.

12. A cyclic silyl pinacole in accordance with claim 7, where R and $R^1$ are phenyl and $R^6$ and $^7$ are methyl and phenyl respectively.

13. A cyclic silyl pinacole in accordance with claim 7 where R and $R^1$ are t-butyl.

* * * * *